United States Patent [19]

Cleary et al.

[11] Patent Number: 4,772,584

[45] Date of Patent: Sep. 20, 1988

[54] INHIBITOR OF C5A-MEDIATED CHEMOTAXIS

[76] Inventors: Paul P. Cleary, 288 Jansa Dr., Shoreview, Minn. 55126; Daniel E. Wexler, 1004 W. County Rd. D, New Brighton, Minn. 55112

[21] Appl. No.: 867,795

[22] Filed: May 23, 1986

[51] Int. Cl.[4] .............................................. A61K 37/02
[52] U.S. Cl. ........................................ 514/2; 530/825; 435/69; 436/86; 436/89
[58] Field of Search ............... 514/2; 530/825; 435/69; 436/86, 89

[56] References Cited

U.S. PATENT DOCUMENTS 3,929,994  12/1975  Hirsch et al. ........................ 424/177

OTHER PUBLICATIONS

Wexler et al., *Proc. Natl. Acad Sci.*, USA, 82, pp. 8144–8148 (Dec. 1985).
P. A. Ward et al., *J. Immunology*, 111, 1771 (1973).
K. J. Johnson et al., *J. Clin. Invest.*, 59, 951 (1977).
P. A. Ward et al., *J. Clin. Invest.*, 58, 123 (1976).
D. E. Wexler et al., *Infection and Immunity*, 39, 239 (1983).
P. P. Cleary et al., *Recent Advances in Streptococci and Steptococcal Diseases*, Y. Kinura et al., eds., Reed Books, Ltd., England (Jul. 1, 1985) at pp. 179–180.

*Primary Examiner*—J. R. Brown
*Assistant Examiner*—F. T. Moezie
*Attorney, Agent, or Firm*—Merchant, Gould, Smith, Edell, Welter & Schmidt

[57] ABSTRACT

Polypeptides are disclosed which inhibit the binding of the C5a chemotaxin to polymorphonuclear leukocytes by cleaving a six amino acid peptide from the carboxy-terminus of the C5a chemotaxin. The polypeptides can be isolated from virulent strains of group A streptococci, *s. pyogenes*, by enzymatic or detergent extraction.

2 Claims, No Drawings

INHIBITOR OF C5A-MEDIATED CHEMOTAXIS

BACKGROUND OF THE INVENTION

The invention was made with Government support by means of Grant No. 20016-04 awarded by the National Institutes of Health. The Government has certain rights in the invention.

The acute inflammatory response depends on the attraction of phagocytic polymorphonuclear leukocytes (PMN) to the site of microbial invasion by a chemotactic stimulus. The C5a chemotaxin is pivotal to the effectuation of this response in humans. C5a is a peptide derived from the fifth component of serum complement during complement activation by an invading microbial pathogen.

C5a is known to mediate various pathological conditions, chronic inflammation, acute pulmonary disorders and even the metastatic spread of cancerous tumors. C5a is chemotactic for neutrophils, monocytes, macrophages, eosinophils and basophils. Thus, this serum factor is an important attractant to leukocytes and is crucial to their accumulation in vivo at sites of immunologic injury. Leukocytes accumulated at a site of inflammation release granular contents, various hydrolytic enzymes and other toxic components into the extracellular spaces. As a result, the surrounding tissue is damaged. Numerous chronic inflammatory diseases are thought to involve the aberrant presence of C5a in tissue. Rheumatoid arthritis, osteoarthritis and psoriasis are a few examples. The lung is particularly vulnerable; excess c5a in circulation or in the lung can result in aggregation and migration of leukocytes into this organ. This can lead to microvascular occlusion, endothelial damage and subsequent edema. In *J. Amer. Med. Soc.*, 244, 199 (1980), Hammerschmidt suggested that noncardiac pulmonary edema associated with transfusion and hemodialysis depend on an abberant increase in circulating C5a.

The in vivo or pharmacologic control of inflammation is presumed to be highly dependent on the modulation of chemotaxis. There are three levels at which chemotactic inhibition can occur: (1) suppression of the leukocytic response to chemotactic stimuli, (2) prevention of chemotaxin generation, and (3) inactivation of the chemotaxins. Most therapeutically useful drugs act on leukocytes to alter their responsiveness to chemotactic stimuli. Likewise, a number of bacterial products are known to suppress the directed and random migration of polymorphonuclear leukocytes. These compounds include staphylococcal cell wall mucopeptide, *C. perfringens* O toxin, and lipopolysaccharides. Various group A streptococcal components also exert cell-directed inhibitory effects. These include streptolysin O, streptokinasestreptodornase, and lipoteichoic acid. However, these bacterial products are highly toxic and lack specificity.

Studies concerning the inactivation of chemotactic factors have primarily concentrated on host mechanisms of self-regulation. Leukocytes release several enzymes which inactivate chemotaxins. These include the myeloperoxidase-hydrogen peroxide-halide system as well as certain azurophilic granular enzymes. Ward et al., in *J. Immunol.*, 111, 177 (1973) have described a serum factor (CFI) which irreversibly inactivates C5a. Johnson et al., in *J. Clin. Invest.*, 59, 951 (1977) have demonstrated that partially-purified CFI is a potent inhibitor of inflammatory reactions triggered by immune complexes in rat models, and have suggested that CFI is an important regulator of inflammation. However, the mechanism of action of CFI remains unknown, and the potential use of CFI as an anti-inflammatory agent is limited by its resistance to purification and the minuscule quantities present in serum.

Other than non-specific proteolytic enzymes, there are no known chemical agents which can specifically alter the chemotactic properties of C5a. Therefore, the only drugs of therapeutic value which have thus far been developed are those which alter the chemotactic responsiveness of inflammatory cells. For example, see S. Klebanoff and R. Clark, in *The Neutrophil: Function and Clinical Disorder*, Elsevier, North-Holland Biochemical Press (1978) at pages 73–160.

In 1983, D. E. Wexler et al., in *Infection and Immunity*, 39, 239 (1983) reported that the incubation of human serum with M+ group A streptococci did not elicit serum chemotactic activity, even though complement was activated to completion. Treatment of the bacteria with trypsin resulted in the release of the inhibitory molecule from the cell surface. The resistance of the chemotactic factor inactivator to pepsin and trypsin indicated that the protease-sensitive M protein was not involved, although the M protein contributes to the ability of group A streptococci to resist host phagocytic defenses. The inhibitory species was not structurally characterized and the chemotactic target as well as the mechanism of inactivation were not elucidated.

Therefore, the need exists for compositions which can inhibit C5a-mediated chemotaxis. Compositions which can transiently regulate the systemic or localized reactivity of C5a have the potential to limit pathophysiologics such as arthritis and other C5a-mediated inflammatory reactions.

BRIEF DESCRIPTION OF THE INVENTION

The present invention is directed to a composition of matter which is a potent inhibitor of the biologic activity of the C5a chemotaxin. The present invention is also directed to a method for the inhibition of the binding of the C5a chemotaxin to leukocytes comprising contacting the chemotaxin with an effective amount of the composition of the invention.

The present composition comprises a substantially-pure polypeptide which incorporates all or a portion of the amino acid sequence of a protein which is expressed in surface-bound form by virulent strains of group A streptococci (*streptococcus pyogenes*), wherein said polypeptide blocks the binding of C5a chemotaxin to polymorphonuclear leukocytes by cleaving a six amino acid peptide from the carboxy-terminus of the C5a chemotaxin. This streptococcal chemotactic factor inactivator polypeptide (hereinafter "SCFI") can be extracted from virulent strains of group A streptococci by chemical or enzymatic methods. Therefore, as used herein, the term "substantially pure" is intended to mean that SCFI has been isolated from its natural association with the bacterial cellular surface and the other factors associated therewith, such as protein M, streptococcal proteinase and the like.

Although the molecular weight of the native SCFI protein has not been established, the procedures of the present invention readily afford a number of polypeptides which attack the carboxy-terminal region of C5a to produce a molecule that lacks the capacity for functional interaction with receptors on polymorphonuclear leukocytes. It is believed that these biologically-active polypeptides are fragments of the native SCFI protein.

Specific embodiments of SCFI include the 135 and 137 Kd (Kilodalton) molecular weight polypeptides derived by the controlled extraction of group A streptococci with trypsin or by the extraction of group A streptococci with a nonionic detergent, and the 120 Kd and 124 Kd polypeptides derived by the extraction of group A streptococci with a zwitterionic detergent.

The biological and chemical properties of SCFI are summarized in Table I, below.

TABLE 1
Biological and Biochemical Properties of SCFI

| | |
|---|---|
| Location: | Outer surface of Group A streptococci (*S. pyogenes*)[1] |
| Distribution: | Specific to *S. pyogenes*, not significantly associated with group B, C, D, F, or G streptococci |
| Activity: | Specific endopeptidolytic cleavage of complement C5a protein |
| Chemical nature: | protein |
| Adsorption maximum: | 276 nm |
| Identifiable: | Polyclonal hyperimmune rabbit serum |
| Extraction: | Mild trypsin, muralytic enzyme and detergents |

[1] Production by M6, M49, M12, M11 and M2 serotypes confirmed (P. Cleary et al., in Recent Advances in Streptococci and Streptococcal Diseases, Y. Kinura et al., eds., Reed Book Ltd., England (1985) at pages 179-180).

Based on ELISA assays, immunodiffusion analysis and neutralization studies with hyperimmune sera, it is believed that SCFI is antigenically identical for all strains and serotypes of group A streptococci.

DETAILED DESCRIPTION OF THE INVENTION

The isolation and characterization of SCFI will be further described by reference to the following detailed examples.

EXAMPLE I - Trypsin Extraction

A. Materials and Methods

1. Streptococcal strain and growth. Strain CS101, virulent M49, T14 group A streptococci were used as the source of SCFI. Bacteria were grown in Todd-Hewitt broth (Difco Laboratories, Detroit, Mich.) supplemented with 2% neopeptone (Difco). One liter of exponential-phase culture was inoculated into 25 liters of growth medium and incubated overnight at 37° C. Bacteria were harvested by continuous-flow centrifugation, and the packed pellet was stored at −20° C. until use.

2. Trypsin extraction. Frozen pellets from four batch cultures of streptococci, totaling 160 g (wet weight), were thawed and washed twice in Sorenson 0.067M phosphate buffer (pH 8.0). Washed bacteria were suspended in 770 ml of the same buffer and incubated with trypsin (type II-0); Sigma Chemical Co., St. Louis, MO, hereinafter "Sigma")(100 µg/ml final concentration) at 37° C. for 90 min with gentle stirring. The bacteria were then pelleted by centrifugation at 13,000×g for 10 min at 4° C. After discarding the pellet, the supernatant was sterilized with a 0.45-µm nitrocellulose membrane (Millipore Corp., Bedford. Mass.).

3. Ammonium sulfate fractionation. Trypsin extract was precipitated at 4° C. by addition of crystalline ammonium sulfate to 55% saturation. After 30 min, the mixture was centrifuged at 13,000×g for 10 min, and the pellet was discarded. The supernatant was adjusted to 90% saturation with ammonium sulfate, and after 30 min, the resulting precipitate was collected by centrifugation. The pellet was suspended in 50 ml of 0.01M sodium phosphate buffer (ph 6.7) containing 30% ammonium sulfate.

4. Hydrophobic interaction chromatography. The salt-fractionated trypsin extract was loaded onto a column (2.1 by 29 cm) of phenylsepharose-CL (Pharmacia Inc., Piscataway, NJ) equilibrated with 0.01M sodium phosphate (ph 6.7)-30% ammonium sulfate. The column was washed with one column volume of equilibration buffer and eluted with a 480 ml linear ammonium sulfate gradient (30 to 0%) at 50 ml/hr. Fractions (4 ml) were analyzed for optical density (at 280 nm) and chemotactic inhibitory activity. SCFI activity (expressed as the reciprocal of the chemotactic differential) was scored at a 1/100 final dilution in 50% ZAS. Salt concentrations were determined from the refractive index.

5. Anion-exchange chromatography. SCFI-containing fractions from the phenylsepharose hydrophobic column were pooled and dialyzed exhaustively against 0.05M Tris- hydrochloride buffer (pH 7.0). The dialyzed pool was loaded onto a DEAE-cellulose anion-exchange column (1.1 by 22 cm; Cellex-D; Bio-Rad Laboratories, Richmond, Calif.) equilibrated in the same buffer as the sample, and the column was eluted with a 200-ml linear gradient of NaCl (0 to 0.5M). The column was run at 11 ml/hr, and fractions (1.0 ml) were analyzed as described above, except that SCFI activity was scored at 1/200 final dilution in 50% ZAS.

6. Gel permeation chromatography. SCFI-containing fractions from the anion-exchange column were pooled and concentrated to 0.8 ml by ultrafiltration with a PM-10 membrane (Amicon Corp., Lexington, Mass.). This material was applied to a Sephacryl-300 column (1.6 by 90 cm; Pharmacia) equilibrated with 0.05M Tris-hydrochloride (pH 7.4)-0.14M NaCl (TBS) and eluted at 7.0 ml/h with the same buffer. Fractions (0.8 ml) were analyzed for optical density (at 280 mn), and SCFI activity was quantitated by serial dilution. Fractions containing ≧200 U of SCFI activity per ml were pooled and stored at −70° C. This material was designated S300 SCFI.

7. PAGGE. Discontinuous sodium dodecyl sulfatepolyacrylamide gradient gel electrophoresis (SDS-PAGGE) was performed by a modification of the Laemmli system [*Nature* (London), 227, 680 (1970)] with an exponential gradient of 5 to 20% acrylamide. Nondenaturing gels for molecular weight comparisons were performed under the same conditions except for the exclusion of SDS and an extended electrophoretic run time of 5.5 hr for pore limit separations [J. Margolis, *Nature* (London), 214, 680 (1967)]. Proteins were visualized in the gels by the silver staining technique of Oakley et al., *Anal. Biochem.*, 105, 361 (1980). Molecular weight standards for SDS gels were cytochrome c, carbonic anhydrase, ovalbumin, bovine serum albumin, β-galactosidase (Sigma), and apoferritin (Schwarz/Mann, Orangeburg, N.Y.).

8. Antiserum preparation. Antisera to S300 SCFI was produced in New Zealand White rabbits by subcutaneous injection of 75 µg of column-purified protein elumsified in Freund complete adjuvant. Subsequent booster injections of 40 µg of protein in incomplete Freund adjuvant were made 4 weeks apart, and rabbits were bled 1 week after each booster. The content of SCFI-specific antibody was assessed by neutralization of SCFI activity and by immunodiffusion analysis.

9. Western blot analysis. SDS-PAGGE gels were electroblotted onto a 0.45-μm (pore size) nitrocellulose membrane (SS BA85; Schleicher and Schuell, Inc., Keene, N.H.) by the method described by Burnette et al., *Anal. Biochem.*, 112, 195 (1981), with the Hoefer Transphor, model TE-50. Protein transfer was carried out at 500 V for 4 hr with cooling in an electrode buffer consisting of 20 mM Tris base, 150 mM glycine, and 20% methanol. After transfer, the nitrocellulose was treated by a modification of the procedure of Blake et al., [*Anal. Biochem.*, 175, 175, (1984)], and all steps were performed at 25° C. The protein blot was immersed in a solution of 3% gelatin-TBS for 45 min, then washed in 0.05% Tween 20-TBS (TTBS) for 45 min. The blot was then probed with a 1:100 dilution of rabbit SCFI antiserum in TTBS for 2 hr and washed three times in TTBS (5 min per wash). The blot was subsequently exposed for 2 hr to alkaline phosphataseconjugated goat anti-rabbit antibody (1:800 in TTBS) (Sigma) and washed sequentially with TTBS, TBS, and 0.015M Veronal acetate buffer (pH 9.6) (twice each). Development of the blot was carried out by immersion for 2 to 5 min at 25° C. in 9 ml of 0.015M Veronal acetate buffer (pH 9.6) containing 1 mg of 5-bromo-4-chloroindoxyl phosphate (Sigma), 1 mg of nitroblue tetrazolium (Sigma), and 4.4 mM $MgCl_2$. Staining was stopped at the desired band intensity by immersion in 10% acetic acid.

10. Chemotaxis inhibition assay for SCFI activity. Chemotactic activity of zymosan-activated serum (ZAS) was measured by the underagarose chemotaxis assay system of Nelson et al. as described in D. E. Wexler et al., *Infect. Immunology*, 39, 239 (1983), the disclosure of which is incorporated by reference herein. Mixed human leukocytes were prepared from heparinized blood by dextran sedimentation as previously described by Wexler et al., supra. Soluble SCFI activity was quantitated by incubating serial twofold dilutions of samples in phosphate-buffered saline (ph 7.4) with an equal volume of ZAS for 60 min at 37° C. ZAS was prepared from serum of a healthy donor who lacked SCFI-specific antibody. The SCFI titer represents the reciprocal of the final dilution which inhibits the directed migration of PMNs to this chemotaxin by 50%. This 50% effective dose for inhibition is expressed as units per milliliter of SCFI activity. Alternatively, SCFI activity was scored by the less quantitative but more rapid method of measuring the decrease in the chemotactic activity of 50% ZAS induced after incubation with a single dilution of a sample within an experiment. In this case, SCFI activity was expressed as the reciprocal of the chemotactic differential (spontaneous distance subtracted from the chemotactic distance).

B. Results

1. Extraction and Purification. Extraction of SCFI (11,000 U of activity) was obtained by incubating bacteria (160 g [wet weight]) at $6 \times 10^{10}$ cells per ml with 0.1 mg of trypsin per ml. After a two-step ammonium sulfate fractionation in which SCFI was precipitated between 55 and 90% salt, most of SCFI activity and 67% of total protein were recovered.

The 55 to 90% ammonium sulfate fraction was chromatographed on a phenylsepharose hydrophobic interaction column, eluting bound material with a decreasingconcentration gradient ammonium sulfate. SCFI activity appeared in fractions having 18 to 10% salt, and the amount of protein in the SCFI pool was reduced approximately fivefold, from 297 to 56 mg. At this point in purification, only trace amounts of phosphate (<0.05 mg) were detectable. The phenylsepharose SCFI pool was dialyzed and fractionated further by ion-exchange chromatography in a DEAE-cellulose column equilibrated at pH 7.0. The anionic nature of SCFI had been previously determined by its ability to bind DEAE-cellulose resin at pH 5.0. Most of the SCFI activity eluted between 0.12 and 0.14M NaCl in a single peak that exhibited a slight trailing edge. The final yield of SCFI activity after this step was 38% of the extracted activity, and this material contained 1.8 mg of protein for 250-fold protein purification. The results of these purification steps are summarized in Table II, below.

TABLE II

Analysis of SCFI Purification Steps

| Purification Step | Protein (mg)[a] | SCFI (U) | Sp act (U mg of protein) |
| --- | --- | --- | --- |
| Trypsin extraction | 441 | 110,600 | 251 |
| Salt Fractionation | 297 | 100,875 | 340 |
| Hydrophobic chromatography | 56 | 62,100 | 1,109 |
| Anion-exchange chromatography | 1.8 | 42,240 | 23,467 |

[a]Measured by the Lowry method with bovine serum albumin as the standard.

2. Characterization of purified SCFI. Gel permeation analysis was performed to provide an estimate of the degree of homogeneity of the SCFI-associated material. The column elution profile demonstrated that the SCFI activity was heterogeneous, since it segregated into two closely spaced peaks. This heterogeneity was reproducible, indicating that the SCFI activity was associated with a minimum of two molecular species that differed in size. A single major absorbance peak was detected, which corresponded with the SCFI-containing fractions.

Spectrophotometric analysis of the S300 pooled material, designated S300 SCFI, indicated an absorption maximum at 276 nm, confirming that this pool contained protein. To further assess the purity and molecular weight of this material, we analyzed S300 SCFI by PAGGE under nondenaturing (no SDS) and denaturing conditions. S300 SCFI electrophoresed in the absence of SDS produced a pattern markedly different from that in the SDS gel. Silver-stained gels of undenatured SCFI revealed three major proteins and no more than four minor components. These peptides most likely differed in size, since the gel was run under the pore limit conditions developed by J. Margolis et al., *Nature* (London), 214, 680 (1967). In contrast, the SDS gel exhibited seven major high-molecular-weight bands ranging from 103,000 to 114,000 $M_r$ and over 50 minor species spanning a wide range of lower molecular weights. The SDS pattern was unaffected by 2-mercaptoethanol, indicating the absence of disulfide bonds.

3. Immunological properties. As described herein above, hyperimmune antiserum was prepared which was able to neutralize SCFI activity, since preincubation of S300 SCFI with the serum resulted in a dose-dependent reduction of antichemotactic activity. Preimmune serum had no effect on activity. The antiserum was highly specific for SCFI, since nondenaturing PAGGE Western blot patterns for crude trypsin extracts were identical to that of the purified material.

The resistance of SCFI to mild pepsin digestion and its relative resistance to trypsin distinguish it from M protein, which is known to be sensitive to both proteases. To test relatedness further, the two antigens were compared by immunodiffusion. Rabbit antiserum specific for SCFI produced a single precipitin arc in reaction to the immunogen, S300 SCFI, or partially purified SCFI extracted from cells with group C streptococcal phage lysin (DEAE-SCFI). In contrast, this antiserum did not react with Lancefield acid extracts known to contain M49 antigen. Moreover, M49 typing serum did not react with either preparation of SCFI but reacted strongly with an acid extract of M49 cells. In addition to immunodiffusion experiments, purified M24, M5, and M6 proteins at 16.0 μg each, were unable to bind competitively to SCFI antibody in enzyme-linked immunosorbent inhibition assays which reproducibly detect 5 ng of SCFI antigen.

EXAMPLE II - Nonionic Detergent Extraction

A. Materials and Methods

1. Extraction of streptococci. A 50-ml culture of M49 bacteria in early exponential phase was inoculated into 2 liters of Todd-Hewitt broth-2% neopeptone and grown to late exponential phase. Bacteria were centrifuged at 13,000×g for 10 min at 4° C. and washed once in Hanks balanced salt solution containing 0.1% gelatin. The bacterial pellet was suspended at $5 \times 10^{10}$ cells per ml in TBS containing 1% Nonidet P-40 (NP-40)(nonylphenoxy)(EtO)$_9$H, Sigma), and the extraction mixture was stirred gently at either 4° or 37° C. for 60 min. After detergent treatment, bacteria were sedimented at 13,000×g for 10 min at 4° C., and the supernatants were filter-sterilized with a 0.45-μm (pore size) nitrocellulose membrane (Millipore). This material is designated SCFI-det.

2. Double immunodiffusion. Double-diffusion analysis in agar was performed by the method of O. Ouchterlony, *Acta. Pathol. Microbiol. Scand.*, 32, 231 (1953). Gels were cast in microscope slides and consisted of 1% noble agar in 0.02M phosphate buffer (pH 7.4). Samples (15 μl) were added to 3 mm wells, and the plates were incubated for 2 hr at 37° C., followed by 18 hr at 24° C. Precipitin reactions were photographed directly without staining.

B. Results

1. Extraction and Purification. M+ bacteria were incubated in buffer containing 1% NP-40 for 1 hr at 4° C. The bacterium-free supernatant, when examined by immunodiffusion with S300 SCFI-specific antiserum, gave a reaction of identity with S300 SCFI antigen. Crude NP-40 extracts were examined by Western blot analysis of SDS-PAGGE gels to determine the size and degree of homogeneity of the SCFI antigen (SCFI-det). NP-40 extract, prepared at either 4° or 37° C., was electrophoresed in duplicate sets on the same gel; one set was Western blotted for detection of SCFI, and the other was silver stained for total extracted protein. The results demonstrated that two antigenic species of similar molecular weight, but of unequal band intensity, were present. The SCFI bands corresponded to two bands on the duplicate silver-stained gel when the blot and stained gel were physically aligned. The two corresponding silver-stained bands also stained unequally and were well separated from bands of lower molecular weight. Their molecular weights were estimated to be 135,000 and 137,000 when compared with protein standards. SCFI-det could be extracted equally well at 4° and 37° C. over the 1 hr incubation period.

2. Characterization. The results of the trypsin extraction procedure for the preparation of SCFI indicated the need for a nonenzymatic method that would be less likely to result in peptide bond cleavage. The ability of the nonionic detergent NP-40 to solubilize SCFI antigen was assessed by immunological analysis of M+ bacterial extracts derived after a short incubation with the detergent at 4° C. Immunodiffusion analysis of this extract indicated that a species was present having antigenic determinants in common with S300 SCFI. Western blots of NP-40 extracts identified a major band of 135,000 $M_r$ (molecular weight) and a less abundant protein of 137,000 $M_r$. Thus, if trypsin and detergent-extracted antigen were derived from the same population of molecules on the bacterial surface, it is likely that the heterogeneity of S300 SCFI is largely an aspect of enzymatic hydrolysis during extraction. The detection of at least five peptide species retaining biological activity by HPLC analysis indicated that limited cleavage of the native protein does not eliminate activity in at least some of the products.

Example III - Inhibition of C5a with S300 SCFI

A. Materials and Methods

1. Preparation of Human C5a and C5a$_{desArg}$. C5a was generated in zymosan-activated human serum containing 1M ε-aminocaproic acid and it was purified according to the procedure of Fernandez and Hugli, *J. Immunol.*, 120, 109 (1978). C5a$_{desArg}$ was purified by the same method except that serum was activated in the absence of ε-aminocaproic acid. Human C5a was radiolabeled with Na$^{125}$I (Amersham) by the solid-phase lactoperoxidase/glucose oxidase method as described by D. E. Chenoweth et al., *J. Exp. Med.*, 156, 68 (1982). $^{125}$I-labeled C5a$_{desArg}$ for analysis by NaDodSO$_4$/P-AGE analysis was obtained from Upjohn (Kalamazoo, MI).

2. Preparation of Human Peripheral Polymorphonuclear Leukocytes (PMNs). Human PMNs were collected by venipuncture of healthy volunteers as described by Boyum, *Scand. J. Clin. Lab. Invest.*, 21, Suppl. 97,77 (1968). After Ficoll-Hypaque centrifugation (*J. Immunol. Methods*, 24, 389 (1978)), the PMN-containing layer was subjected to hypotonic lysis in 0.87% NH$_4$Cl to remove contaminating erythrocytes by the method of Goldstein et al., *J. Immunol.*, 111, 33 (1973). The PMNs were harvested by centrifugation at 150×g for 10 min, washed twice in 0.9% NaCl, and resuspended to the appropriate cell density in RPMI (GIBCO) tissue culture medium containing 1% bovine serum albumin.

3. C5a Binding assay. Binding of $^{125}$I-labeled C5a to PMNs was assessed by mixing $4 \times 10^6$ PMNs per ml in RPMI medium/1% bovine serum albumin with $^{125}$I-labeled C5a at a final concentration of 1 nM in a 0.1-ml vol. The mixtures were incubated for 15 min at 24° C. in 1.5-ml conical polypropylene microfuge tubes followed by centrifugation at 11,000×g for 30 sec in a Beckman Microfuge B. The amount of cell-bound $^{125}$I-labeled C5a was determined by transferring one-half of the PMN-free supernatant to a separate tube and comparing the γ radioactivity of the paired samples P (pelleted cells + one-half supernatant) and S (one-half supernatant). Cell-bound $^{125}$I-labeled C5a was calculated according to the following equation:

$$\% \text{ bound} = \frac{\text{cpm}(S + P) - NS \text{ cpm}(S)}{\text{cpm}(S + P)} \times 100$$

NS, nonspecific binding to the assay tube, was cpm(P+S)/cpm(S). Of the total ligand, 30-50% was PMN-associated under these conditions.

4. Amino acid analysis. For determination of free amino acids, unhydrolyzed samples or 2 nmol of hydrolyzed C5a standard were examined by using a Durrum amino acid analyzer. Hydrolysis of C5a was done in 5.6 M HCl by heating in a vacuum-sealed ampoule at 100° C. for 18 hr.

5. Carboxyl-terminal analysis. C5a$_{desArg}$ (1 nmol) or purified SCFI-inactivated C5a in 0.1 M NH$_4$HCO$_3$ (pH 8.15) was digested with 0.1 nmol of carboxypeptidase A (phenylmethylsulfonyl fluoride-treated)(Worthington) and 0.1 nmol of carboxypeptidase B (Calbiochem) for 4.5 hr at 37° C. These samples were lyophilized and analyzed for free amino acids in the absence of hydrolysis as described above.

6. NaDodSO$_4$/PAGE. Discontinuous polyacrylamide gel electrophoresis was carried out under reducing conditions by a modification of the procedure of Example I(A)(7), supra. For electrophoresis of $^{125}$I-labeled C5a$_{desArg}$, a separation gel was used consisting of an exponential gradient of 15-20% acrylamide (12-16% glycerol) and radiolabeled protein visualized by autoradiography with Kodak XAR-5 x-ray film. Denatured bovine serum albumin was prepared by a modification of the alkaline urea method of Anson, *J. Gen. Physiol.*, 22, 79 (1938). Bovine serum albumin (50 μg) in H$_2$O was first incubated with 50 mM dithiothreitol for 10 min at room temperature, then the protein was alkalinized with NaOH (0.08 M final NaOH concentration). Crystalline urea was added to 7.3 M, and the mixture was incubated at room temperature for 1 hr. The denatured bovine serum albumin was diluted with an equal volume of 0.062 M Tris.HCl(pH 7.4) and dialyzed overnight against the same buffer. A 5-15% acrylamide gradient was used for electrophoresis of bovine serum albumin (Sigma), and silver staining was by the Oakley method *(Anal. Biochem.,* 105, 61 (1980)).

B. Results

1. Inactivation of $^{125}$I-labeled C5a by SCFI. The concentration-dependent effect of S300 SCFI on the PMN receptor binding and the antigenic properties of $^{125}$I-labeled C5a were assessed. S300 SCFI, ranging in concentration from 0 to 625 ng/ml, was incubated with 5 nM $^{125}$I-labeled C5a (41 ng/ml) for 60 min at 37° C., and the ability of treated ligand to bind PMNs was measured. Specific PMN binding of $^{125}$I-labeled C5a was completely inhibited by prior incubation of the C5a with SCFI (10 ng/ml), and as little as 0.07 ng of SCFI per ml produced a significant binding inhibition. This represents a weight ratio of C5a to SCFI of about 600-4:1. The possibility that this effect was due to the complete destruction of C5a by either SCFI or enzymatic contaminants of the SCFI preparation was highly unlikely because the antigenicity of the $^{125}$I-labeled C5a remained unaltered.

2. Proteolytic Cleavage of C5a by SCFI. NaDodSO$^4$/PAGE analysis was performed to determine whether inactivation of $^{125}$I-labeled C5a$_{desArg}$ by SCFI was accompanied by a decrease in molecular weight, as would be expected from enzymatic cleavage of the molecule. $^{125}$I-labeled C5a$_{desArg}$ incubated with SCFI exhibited a significantly greater electrophoretic mobility than untreated $^{125}$I-labeled C5a$_{desArg}$. This difference in mobility was small, corresponding to a M$_r$ of about −500, suggesting that SCFI mediates the cleavage of $^{125}$I-labeled C5a$_{desArg}$ near the amino or carboxyl terminus.

To locate the peptide bond in C5a that is cleaved by SCFI, the carboxyl-terminal sequence of immunoaffinity-purified SCFI-inactivated C5a was compared with that of native C5a$_{desArg}$. Under partial digestion conditions, the relative amount of each amino acid released by carboxypeptidases A and B depends on its distance from the COOH terminus of the peptide in question. Because the sequence of C5a is known, this approach unequivocally identifies the COOH-terminal residue. The results presented in Table III demonstrate that SCFI-inactivated C5a lacks the end sequence -Asp$^{69}$-Met$^{70}$-Gln$^{71}$-Leu$^{72}$-Gly$^{73}$-Arg$^{74}$, and therefore, C5a cleavage occurs between Lys$^{68}$ and Asp$^{69}$.

TABLE III

| | Carboxyl-terminal analysis of SCFI-inactivated C5a | |
|---|---|---|
| Amino acid | C5a$_{desArg}$, nmol | SCFI-inactivated C5a*, nmol |
| Gly | 1.06 | 0.11 |
| Leu | 0.86 | 0.06 |
| Glx | 0.85 | 0.02 |
| Met | 0.37 | 0.00 |
| Asx | 0.32 | 0.00 |
| Lys | 0.32 | 1.00 |
| His | 0.28 | 1.12 |
| Ser | 0.00 | 0.67 |
| Ile | 0.13 | 0.19 |
| Phe | 0.12 | 0.26 |
| Tyr | 0.15 | 0.78 |
| Thr | 0.06 | 0.36 |

Known Sequence:
```
           65                    68                    71
  —Asn—Ile—Ser—His—Lys—Asp—Met—Gln
C5a_desArg, nmol         0.28 0.32 0.32 0.37 .085
SCFI-C5a, nmol      0.67 1.12 1.00

74
              —Leu—Gly—(Arg)—COOH
C5a_desArg, nmol 0.86 1.06
SCFI-C5a, nmol    —    —
```

*One nanomole of carboxypeptidase-digested C5a$_{desArg}$ or SCFI-inactivated C5a was analyzed. SCFI inactivation was assessed by the reduction in ligand-receptor binding affinity.

EXAMPLE IV - Zwitterionic Detergent Extraction 1-10 l batches of a group A streptococcal culture, strain CS101 serotype M49, T14, are grown to log phase in Todd-Hewitt broth supplemented with neopeptone at 37° C. At log phase, cells are harvested, washed with 0.1 M Na$_2$HPO$_4$, pH 7.4 buffer and resuspended in an extraction buffer to a final concentration of 0.1 M Na$_2$HPO$_4$, 0.5% ((3-[3-cholamidopropyl)-dimethylammonio]-1-propanesulfonate, "CHAPS," Sigma), with 10 μg/ml DNAse, 10 μg/ml RNAse, 75 μg/ml phenylmethylsulfonyl fluoride, (PMSF) and 1.0 mM sodium iodoacetate.

The suspension is stirred for 90 min at 42° C., centrifuged and the pellet discarded. The supernatant (the crude extract) is concentrated and then applied to a Sephadex G-50-300 column. The column is equilibrated and eluted with 0.05M Tris.HCl, pH 7.0. Fractions containing SCFI are pooled and applied directly to a cellulose QAE anion exchange column. This column is eluted with an increasing linear salt gradient from 0.05M Tris.HCl, pH 7.0 to 0.5M Tris.HCl/0.5M NaCl, pH 7.0. Fractions containing the SCFI are pooled, adjusted to a 30% saturation of $(NH_4)_2SO_4$, applied to a Phenyl Sepharose CL-4B column and eluted with a decreasing linear salt gradient from 0.05M Tris.HCl/30% $(NH_4)_2SO_4$, pH 7.0 to 0.05M Tris.HCl, pH 7.0. Fractions containing SCFI are pooled, desalted by and concentrated to yield a pure preparation.

SCFI isolated and purified by the above procedure comprises primarily two peptides when analyzed by SDS PAGGE electrophoresis, which were estimated to have molecular weights of 124 Kd and 120 Kd. This mixture of peptides also exhibits a spectrum of activity with respect to C5a which is essentially similar to the activity of S300 SCFI as determined hereinabove.

DISCUSSION

The results of the present study show that the streptococcal chemotactic factor inactivator polypeptide of the present invention (SCFI) is a protease that attacks the COOH-terminal region of C5a at the carboxyl side of a lysine residue to produce a molecule that lacks the capacity for functional interaction with PMN receptors. SCFI-inactivated C5a is similar to the reaction product of C5a with yeast carboxypeptidase Y, C5a-(1-69), in lacking COOH-terminal residues required for receptor stimulation. However, distinctions between SCFI-inactivated C5a and C5a-(1-69) exist on both structural and mechanistic levels. The product of SCFI hydrolysis lacks six COOH-terminal amino acid residues as the result of cleavage between $Lys^{68}$ and $Asp^{69}$; this contrasts with the five-residue loss in the carboxypeptidase Y C5a derivative. Moreover, on the basis of its activity against denatured bovine serum albumin, SCFI appears to cleave C5a by an endoprotease activity as opposed to the sequential hydrolysis of peptide bonds characteristic of carboxypeptidases. SCFI also appears to be highly site-selective because, aside from the loss of the six carboxyl-terminal residues, the C5a residue was largely intact. This latter conclusion is based on the detection in purified SCFI-inactivated C5a of a single carboxyl terminus and, therefore, one polypeptide chain, as well as $NaDodSO_4$/PAGE analysis indicating that the decrease in molecular weight of the C5a was quite small ($M_r$, about 500).

In summary, the potential of group A streptococci to inactivate serum chemotactic activity is mediated by a surface-bound protein that exhibits a high degree of specificity for the C5a chemotaxin. In accordance with the present invention, this protein or the polypeptide fragments thereof, can be extracted from group A streptococci in essentially pure form. The purified compounds retain the ability of the native protein to block the binding of C5a to polymorphonuclear leukocytes by the proteolytic degradation thereof. It is expected that these purified polypeptides will be useful for the investigation of the human immune response, and may provide the basis for therapeutic agents for the treatment of human and animal pathologies mediated by C5a.

While certain representative embodiments of the invention have been described herein for purposes of illustration, it will be apparent to those skilled in the art that modifications therein may be made without departing from the spirit and scope of the invention. For example, although SCFI has been described primarily in terms of the polypeptides designated "S300 SCFI" and the 120 Kd and the 124 Kd polypeptides derived by trypsin and detergent extraction of group A streptococci, any polypeptide which includes a common amino acid sequence and which deactivates C5a by a similar biological pathway is intended to be included within the scope of the present invention.

What is claimed is:

1. A method for the inhibition of the binding of C5a chemotaxin to leukocytes comprising contacting said C5a chemotaxin with an effective amount of a polypeptide which is expressed in surface-bound form by streptococcus pyogenes, wherein said polypeptide having a molecular weight of about 120Kd to about 137Kd and inhibits the binding of C5a chemotaxin to polymorphonuclear leukocytes by cleaving a six amino acid peptide from the carboxy-terminus of the C5a chemotaxin.

2. The method of claim 1 wherein the weight ratio of C5a chemotaxin to the polypeptide is about 4-600:1.

* * * * *

UNITED STATES PATENT AND TRADEMARK OFFICE
CERTIFICATE OF CORRECTION

PATENT NO. : 4,772,584

DATED : September 20, 1988

INVENTOR(S) : Paul P. Cleary and Daniel E. Wexler

It is certified that error appears in the above-identified patent and that said Letters Patent is hereby corrected as shown below:

At Title Page, insert --[73] Assignee: Regents of the University of Minnesota, Minneapolis, Minnesota.--.

At Col. 1, line 32, for "c5a" read --C5a--.

At Col. 3, line 59, for "hereinafter" read --(hereinafter--.

At Col. 4, line 41, "280 mn" read --280 nm--.

At Col. 4, lines 64-65, for "elumsified" read --emulsified--.

Signed and Sealed this

Fourth Day of July, 1989

Attest:

DONALD J. QUIGG

Attesting Officer

Commissioner of Patents and Trademarks